United States Patent
Reilly (12)

(10) Patent No.: US 6,958,053 B1
(45) Date of Patent: Oct. 25, 2005

(54) INJECTOR PROVIDING DRIVE MEMBER ADVANCEMENT AND ENGAGEMENT WITH SYRINGE PLUNGER, AND METHOD OF CONNECTING A SYRINGE TO AN INJECTOR

(75) Inventor: David M. Reilly, Glenshaw, PA (US)

(73) Assignee: Medrad, Inc., Indianola, PA (US)

( * ) Notice: Subject to any disclaimer, the term of this patent is extended or adjusted under 35 U.S.C. 154(b) by 0 days.

(21) Appl. No.: 09/448,835

(22) Filed: Nov. 24, 1999

(51) Int. Cl.[7] ............................................. A61M 37/00
(52) U.S. Cl. .......... 604/154; 128/DIG. 1; 128/DIG. 12
(58) Field of Search ................... 604/111, 118, 131, 604/189, 154, 151, 218, 49, 65, 67, 93.01, 604/121, 152, 181, 187, 533, 534, 535; 235/375, 235/435, 448, 454, 462; 116/227; 128/DIG. 1, 128/DIG. 12; 600/431, 432

(56) References Cited

U.S. PATENT DOCUMENTS

| | | |
|---|---|---|
| 1,988,480 A | 1/1935 | Campkin |
| 2,702,547 A | 2/1955 | Glass |
| 3,051,173 A | 8/1962 | Johnson et al. |
| 3,604,417 A | 9/1971 | Stolzenberg |
| 3,623,474 A | 11/1971 | Heilman et al. |
| 3,645,262 A | 2/1972 | Harrigan |
| 3,701,345 A | 10/1972 | Heilman et al. |
| 3,720,211 A | 3/1973 | Kyrias |
| 3,738,539 A | 6/1973 | Beich |
| 3,752,145 A | 8/1973 | Runnells et al. |
| 3,796,218 A | 3/1974 | Burke et al. |
| 3,812,843 A | 5/1974 | Wootten et al |
| 3,964,139 A | 6/1976 | Kleinmann et al. |
| 3,987,940 A | 10/1976 | Tischlinger |
| 4,006,736 A | 2/1977 | Kranys et al. |
| 4,030,498 A | 6/1977 | Tompkins |
| 4,080,967 A | 3/1978 | O'Leary |
| 4,155,490 A | 5/1979 | Glenn |
| 4,226,236 A | 10/1980 | Genese |
| 4,252,118 A | 2/1981 | Richard et al. |
| 4,278,086 A | 7/1981 | Hodgins et al. |

(Continued)

FOREIGN PATENT DOCUMENTS

DE  29 19 978  11/1980

(Continued)

OTHER PUBLICATIONS

Liebel-Flarsheim Company, Angiomat 6000 Digital Injection System Operator's Manual, 600950 Rev 1 (1990); pp. 3-6 to 3-8, 4-52 to 4-56.

(Continued)

*Primary Examiner*—Nicholas D. Lucchesi
*Assistant Examiner*—Mark K. Han
(74) *Attorney, Agent, or Firm*—Gregory L. Bradley; James R. Stevenson; Henry E. Bartony, Jr.

(57) ABSTRACT

An injector for injecting a fluid from a syringe (which syringe includes a body, a plunger moveably positioned within the body, and an encoding device providing syringe information)r includes a housing, a motor disposed within the housing, a controller operably associated with the motor, a sensor operably associated with the controller and operable to read the encoded syringe information provided by the encoding device when the syringe is attached to the injector, a drive member disposed in the housing and powered by the motor, the drive member operable to automatically advance and engage the plunger when the sensor reads the syringe information provided by the encoding device, and a plunger engagement detection device operably associated with the controller and operable to indicate when the drive member of the injector has engaged the plunger of the syringe.

45 Claims, 11 Drawing Sheets

U.S. PATENT DOCUMENTS

| | | |
|---|---|---|
| 4,345,595 A | 8/1982 | Whitney et al. |
| 4,351,332 A | 9/1982 | Whitney et al. |
| 4,356,822 A | 11/1982 | Winstead-Hall |
| 4,424,720 A | 1/1984 | Bucchianeri |
| 4,452,251 A | 6/1984 | Heilman |
| 4,453,934 A | 6/1984 | Gahwiler et al. |
| 4,464,265 A | 8/1984 | Joyner |
| 4,465,472 A | 8/1984 | Urbaniak |
| 4,465,473 A | 8/1984 | Ruegg |
| 4,475,666 A | 10/1984 | Bilbrey et al. |
| 4,476,381 A | 10/1984 | Rubin |
| 4,493,646 A | 1/1985 | Lacour et al. |
| 4,529,401 A | 7/1985 | Leslie et al. |
| 4,568,335 A | 2/1986 | Updike et al. |
| 4,573,978 A | 3/1986 | Reilly |
| 4,585,439 A | 4/1986 | Michel |
| 4,604,847 A | 8/1986 | Moulding, Jr. et al. |
| 4,612,010 A | 9/1986 | Hamacher et al. |
| 4,617,016 A | 10/1986 | Blomberg |
| 4,636,198 A | 1/1987 | Stade |
| 4,648,872 A | 3/1987 | Kamen |
| 4,650,475 A | 3/1987 | Smith et al. |
| 4,652,260 A | 3/1987 | Fenton, Jr. et al. |
| 4,664,128 A | 5/1987 | Lee |
| 4,676,776 A | 6/1987 | Howson |
| 4,677,980 A | 7/1987 | Reilly et al. |
| 4,681,566 A | 7/1987 | Fenton, Jr. et al. |
| 4,685,903 A | 8/1987 | Cable et al. |
| 4,695,271 A | 9/1987 | Goethel |
| 4,705,509 A | 11/1987 | Stade |
| 4,722,734 A | 2/1988 | Kolln |
| 4,741,732 A | 5/1988 | Crankshaw et al. |
| 4,741,736 A | 5/1988 | Brown |
| 4,749,109 A | 6/1988 | Kamen |
| 4,755,172 A | 7/1988 | Baldwin |
| 4,767,406 A | 8/1988 | Wadham et al. |
| 4,773,900 A | 9/1988 | Cochran |
| 4,838,857 A | 6/1989 | Strowe et al. |
| 4,840,616 A | 6/1989 | Banks |
| 4,842,581 A | 6/1989 | Davis |
| RE32,974 E | 7/1989 | Porat et al. |
| 4,853,521 A | 8/1989 | Claeys et al. |
| 4,854,324 A | 8/1989 | Hirschman et al. |
| 4,869,720 A | 9/1989 | Chernack |
| 4,878,896 A | 11/1989 | Garrison et al. |
| 4,911,695 A | 3/1990 | Lindner |
| 4,929,238 A | 5/1990 | Baum |
| 4,936,833 A | 6/1990 | Sams |
| 4,943,279 A | 7/1990 | Samiotes et al. |
| 4,966,601 A | 10/1990 | Draenert |
| 4,969,874 A | 11/1990 | Michel et al. |
| 4,973,309 A | 11/1990 | Sultan |
| 4,978,335 A | 12/1990 | Arthur, III |
| 4,988,337 A | 1/1991 | Ito |
| 5,007,904 A | 4/1991 | Densmore et al. |
| 5,033,650 A | 7/1991 | Colin et al. |
| 5,034,004 A | 7/1991 | Crankshaw |
| 5,047,014 A | 9/1991 | Mosebach et al. |
| 5,078,683 A | 1/1992 | Sancoff et al. |
| 5,084,017 A | 1/1992 | Maffetone |
| 5,085,638 A | 2/1992 | Farbstein et al. |
| 5,085,643 A | 2/1992 | Larkin et al. |
| 5,093,079 A | 3/1992 | Bakaitis et al. |
| 5,104,374 A | 4/1992 | Bishko et al. |
| 5,106,379 A | 4/1992 | Leap |
| 5,135,507 A | 8/1992 | Haber et al. |
| 5,147,311 A | 9/1992 | Pickhard |
| 5,153,827 A | 10/1992 | Coutre et al. |
| 5,226,897 A | 7/1993 | Nevens et al. |
| 5,236,416 A | 8/1993 | McDaniel et al. |
| 5,242,408 A | 9/1993 | Jhuboo et al. |
| 5,254,086 A | 10/1993 | Palmer et al. |
| 5,254,101 A | 10/1993 | Trombley, III |
| 5,256,157 A | 10/1993 | Samiotes et al. |
| 5,269,762 A | 12/1993 | Armbruster et al. |
| 5,275,582 A | 1/1994 | Wimmer |
| 5,279,569 A | 1/1994 | Neer et al. |
| 5,282,792 A | 2/1994 | Imbert |
| 5,300,031 A | 4/1994 | Neer et al. |
| 5,317,506 A | 5/1994 | Coutre et al. |
| 5,324,273 A | 6/1994 | Discko, Jr. |
| 5,338,309 A | 8/1994 | Imbert |
| 5,342,298 A | 8/1994 | Michaels et al. |
| 5,354,287 A | 10/1994 | Wacks |
| 5,356,375 A | 10/1994 | Higley |
| 5,356,393 A | 10/1994 | Haber et al. |
| 5,383,858 A * | 1/1995 | Reilly et al. ............... 604/131 |
| 5,425,716 A | 6/1995 | Kawasaki et al. |
| 5,429,602 A | 7/1995 | Hauser |
| 5,429,611 A | 7/1995 | Rait |
| 5,431,627 A | 7/1995 | Pastrone et al. |
| 5,433,712 A | 7/1995 | Stiles et al. |
| 5,439,452 A | 8/1995 | McCarty |
| 5,445,622 A * | 8/1995 | Brown .................... 604/246 |
| 5,451,211 A | 9/1995 | Neer et al. |
| 5,456,670 A | 10/1995 | Neer et al. |
| 5,520,653 A | 5/1996 | Reilly et al. |
| 5,531,698 A | 7/1996 | Olsen |
| 5,533,981 A | 7/1996 | Mandro et al. |
| 5,535,746 A | 7/1996 | Hoover et al. |
| 5,545,140 A | 8/1996 | Conero et al. |
| 5,573,515 A | 11/1996 | Wilson et al. |
| 5,658,261 A | 8/1997 | Neer et al. |
| 5,662,612 A | 9/1997 | Niehoff |
| 5,681,285 A | 10/1997 | Ford et al. |
| 5,681,286 A | 10/1997 | Niehoff |
| 5,683,367 A | 11/1997 | Jordan et al. |
| 5,738,659 A | 4/1998 | Neer et al. |
| 5,741,227 A | 4/1998 | Sealfon |
| 5,741,232 A * | 4/1998 | Reilly et al. ............... 604/131 |
| 5,779,675 A | 7/1998 | Reilly et al. |
| 5,795,333 A | 8/1998 | Reilly et al. |
| 5,808,203 A | 9/1998 | Nolan, Jr. et al. |
| 5,827,219 A | 10/1998 | Uber, III et al. |
| 5,865,805 A | 2/1999 | Ziemba |
| 5,873,861 A | 2/1999 | Hitchins et al. |
| 5,882,343 A | 3/1999 | Wilson et al. |
| 5,899,885 A | 5/1999 | Reilly et al. |
| 5,913,844 A | 6/1999 | Ziemba et al. |
| 5,919,167 A | 7/1999 | Mulhauser et al. |
| 5,938,639 A | 8/1999 | Reilly et al. |
| 5,944,694 A | 8/1999 | Hitchins et al. |
| 5,947,929 A | 9/1999 | Trull |
| 5,947,935 A | 9/1999 | Rhinehart et al. |
| 5,954,697 A | 9/1999 | Srisathapat et al. |
| 5,954,700 A | 9/1999 | Kovelman |
| 5,997,502 A * | 12/1999 | Reilly et al. ........... 128/DIG. 1 |
| 6,048,334 A | 4/2000 | Hirschman et al. |
| 6,059,756 A | 5/2000 | Yeh |
| 6,080,136 A | 6/2000 | Trull et al. |
| 6,083,197 A | 7/2000 | Umbaugh |
| 6,090,064 A * | 7/2000 | Reilly et al. ........... 128/DIG. 1 |
| 6,099,502 A | 8/2000 | Duchon et al. |
| 6,221,045 B1 | 4/2001 | Duchon et al. |
| RE37,487 E | 12/2001 | Reilly et al. |
| 6,336,913 B1 | 1/2002 | Spohn et al. |
| 6,585,700 B1 | 7/2003 | Trocki et al. |
| 2002/0068905 A1 | 6/2002 | Cowan et al. |
| 2002/0165491 A1 | 11/2002 | Reilly |
| 2002/0177811 A1 | 11/2002 | Reilly et al. |
| 2003/0060754 A1 | 3/2003 | Reilly et al. |

FOREIGN PATENT DOCUMENTS

| | | |
|---|---|---|
| DE | 32 27 417 | 2/1983 |
| DE | 40 17 920 | 12/1991 |
| DE | 196 01 214 | 8/1996 |
| DE | 196 33 530 | 2/1998 |
| EP | 0 160 303 | 11/1985 |
| EP | 0 164 904 | 12/1985 |
| EP | 0 320 168 | 6/1989 |
| EP | 0 323 321 | 7/1989 |
| EP | 0 346 950 | 12/1989 |
| EP | 0 364 010 | 4/1990 |
| EP | 0 384 657 | 8/1990 |
| EP | 0 482 677 | 4/1992 |
| EP | 0 523 343 | 1/1993 |
| EP | 0 567 944 | 11/1993 |
| EP | 0 584 531 | 3/1994 |
| EP | 0 736 306 | 10/1996 |
| EP | 0 749 757 | 12/1996 |
| EP | 0 900 573 | 3/1999 |
| EP | 0 919 251 | 6/1999 |
| GB | 847 914 | 1/1961 |
| GB | 1 380 873 | 1/1975 |
| GB | 2 108 852 | 5/1983 |
| JP | 61-500415 | 3/1986 |
| JP | 63-68177 | 3/1988 |
| WO | WO 80/02376 | 11/1980 |
| WO | WO 85/00292 | 1/1985 |
| WO | WO 85/02256 | 5/1985 |
| WO | WO 89/06145 | 7/1989 |
| WO | WO 89/09071 | 10/1989 |
| WO | WO 89/11310 | 11/1989 |
| WO | WO 90/01962 | 3/1990 |
| WO | WO 91/04759 | 4/1991 |
| WO | WO 92/21391 | 12/1992 |
| WO | WO 94/25089 | 11/1994 |
| WO | WO 96/32975 | 10/1996 |
| WO | WO 97/36635 | 10/1997 |
| WO | WO 99/65548 | 12/1999 |
| WO | WO 01/37905 | 5/2001 |
| WO | WO 02/04049 | 1/2002 |

OTHER PUBLICATIONS

Brochure for "Angiomat 6000" of Liebel-Flarsheim, 2111 E. Galbraith Road, Cincinnati, OH 45215, copyright 1987.

Brochure for "Angiomat CT" of Liebel-Flarsheim, 2111 E. Galbraith Road, Cincinnati, OH 45215, Copyright 1988.

Brochure for "PercuPump 1A" of E-Z-EM, Inc., 717 Main Street, Westbury, NY 11590, Copyright 1990.

Medrad, Mark V/Mark V Plus Injector Operation Manual, KMP 805P Rev. B (1990); pp. 1-18 to 1-28, 3-7 to 3-13, 14-1 to 14-4.

Brochure for the "The First and Only True Injection System," Medrad Mark V System, Control No. 85106-00-BA-02, Nov. 1988.

Medrad Envision CT Injector Operation Manual, EOM 700E, 92401-T-123 Rev E, Copyright 1995.

Injektron 82 MRT User Instructions, Version MR2, CE0535, Med-Tron GmbH (Mar. 10, 1999).

Brochure for "Cordis Lymphography Injector," Cordis Corporation, Miami, FL 33137 (1972).

Medrad Envision CT Injector Operation Manual, EOM 700E, 92401-T-123 Rev E, pp. 2-10 to 2-11 and pp. 2-30 to 2-35 (Copyright 1995).

International Search Report for Counterpart PCT Application PCT/US00/32271.

International Search Report for PCT Application PCT/US03/17305.

International Search Report for PCT Application PCT/AU01/00830.

U.S. Appl. No. 10/166,848, filed Jun. 10, 2002.
U.S. Appl. No. 10/287,167 filed Nov. 4, 2002.
U.S. Appl. No. 10/174,639 filed Jun. 19, 2002.
U.S. Appl. No. 10/619,137 filed Jul. 14, 2003.
U.S. Appl. No. 10/668,643 filed Sep. 23, 2003.
U.S. Appl. No. 10/668,673 filed Sep. 23, 2003.
U.S. Appl. No. 10/669,144 filed Sep. 23, 2003.
U.S. Appl. No. 10/669,148 filed Sep. 23, 2003.
U.S. Appl. No. 10/670,154 filed Sep. 23, 2003.
U.S. Appl. No. 10/380,188 filed Mar. 10, 2003.
U.S. Appl. No. 10/159,592 filed May 30, 2002.
U.S. Appl. No. 10/606,157 filed Jun. 25, 2003.
U.S. Appl. No. 10/722,370 filed Nov. 25, 2003.

* cited by examiner

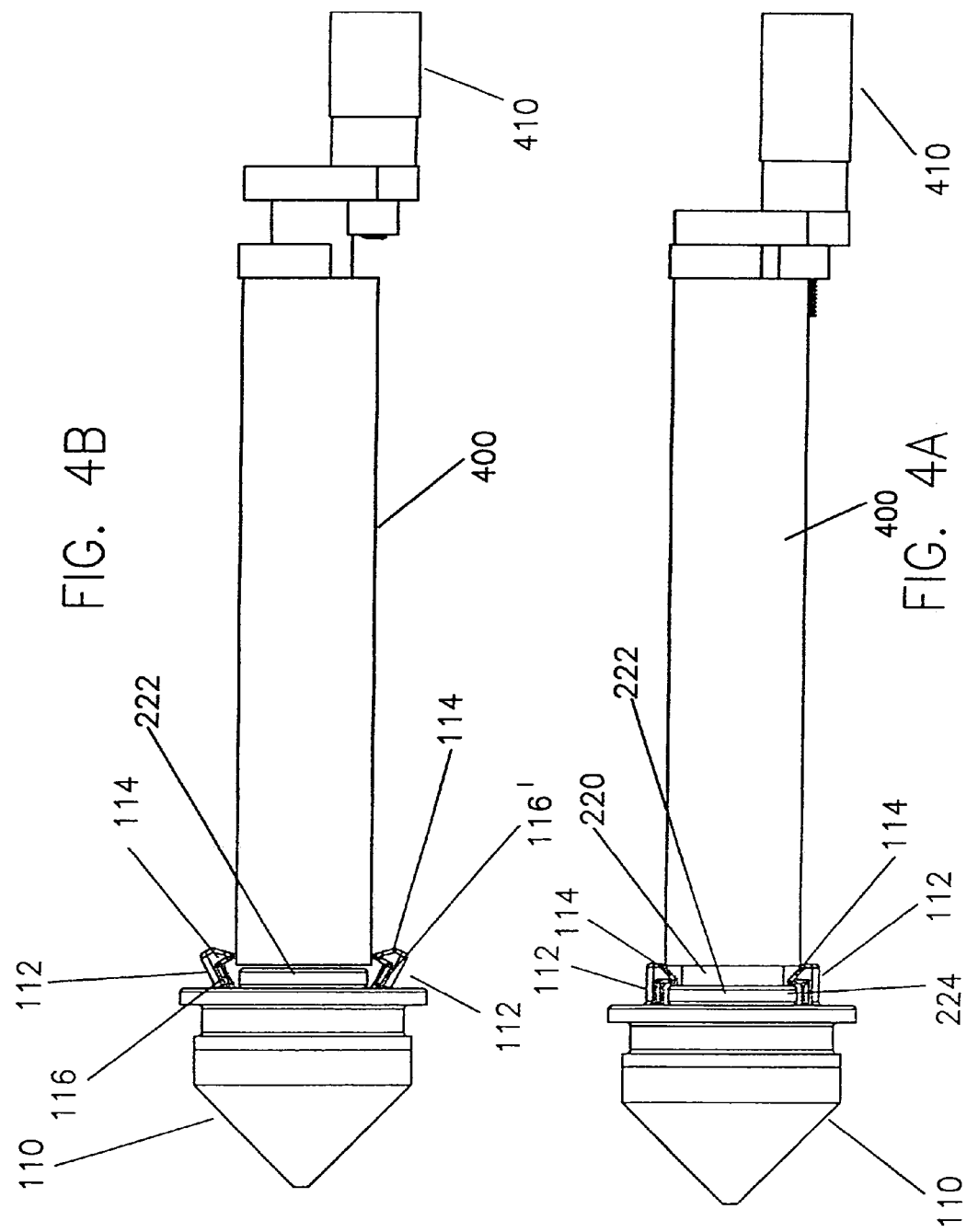

US 6,958,053 B1

INJECTOR PROVIDING DRIVE MEMBER ADVANCEMENT AND ENGAGEMENT WITH SYRINGE PLUNGER, AND METHOD OF CONNECTING A SYRINGE TO AN INJECTOR

FIELD OF THE INVENTION

The present invention relates to injectors and injector systems, and, more particularly, to injectors and injector systems in which a syringe is connected to or loaded upon the injector in a powered or manual manner.

BACKGROUND OF THE INVENTION

A number of injector-actuated syringes and powered injectors for use in medical procedures such as angiography, computed tomography and NMR/MRI have been developed. For example, U.S. Pat. No. 4,006,736 discloses an apparatus for injecting fluid into the vascular system of a human being or an animal. Likewise, U.S. Pat. No. 4,677,980 discloses an angiographic injector and syringe wherein the drive member of the injector can be connected to, or disconnected from, the syringe plunger at any point along the travel path of the plunger via a releasable mechanism requiring rotation of the syringe plunger relative to the piston. Each of the injectors disclosed in U.S. Pat. Nos. 4,006,736 and 4,677,980 includes a pressure jacket that is breach or rear loaded with a syringe.

U.S. Pat. No. 5,300,031 discloses an injector system in which a syringe is loadable in and unloadable from a pressure jacket of an injector through an open front end in the pressure jacket. The injector system of U.S. Pat. No. 5,300,031 permits replacement of a syringe without retraction of the syringe plunger drive or disconnection of injection tubing connected to the syringe.

A front-loading syringe and injector system is disclosed in U.S. Pat. No. 5,383,858. The syringes disclosed in U.S. Pat. No. 5,383,858 can be readily and securely front-loaded directly and accurately on the injector or on a pressure jacket attached to the injector, thereby facilitating the loading-unloading operation as compared to prior systems. In the front-loading system of U.S. Pat. No. 5,383,858 and other currently available front loading systems, a user manually aligns the syringe in a desired orientation relative to the injector and manually inserts and locks the syringe in place.

In the system of U.S. Pat. No. 5,383,858, for example, an interlocking, releasable mechanism is activated and released upon proper axial and radial alignment and subsequent manual rotation of a rearward portion of a syringe relative to a front wall of the injector housing. In one embodiment, the releasable mechanism includes slots on the front wall of the housing for receiving retaining flanges on the rearward end of the syringe. The syringe is manually rotatable to engage the retaining flanges with associated or cooperating flanges on the injector mounting mechanism. The releasable mechanism also includes an annular sealing member on the injector housing front wall against which a resilient annular sealing member or flange on the syringe becomes seated as the syringe is positioned on the mounting mechanism. The resilient annular sealing member and the retaining flanges on the syringe receive the flanges on the injector mounting mechanism therebetween with an interference fit.

The syringe plunger of U.S. Pat. No. 5,383,858 must be appropriately axially and radially positioned relative to the drive member during loading of the syringe upon that injector system so that rotation of the syringe during loading will also cause engagement of the drive member and the syringe plunger.

Although front-loading syringes represent a significant advancement in the area of injector-actuated syringes and powered injectors for use therewith, the loading and unloading procedures therewith require significant operator time/involvement to ensure secure engagement. For example, the operator must ensure that the syringes of current front-loading systems are first properly aligned with and then securely connected to the injector and that the plunger is engaged by the injector drive member. These steps can require substantial time, dexterity and strength as a result of, for example, alignment requirements, awkward and complex motions and close design tolerances. In many cases the injector may also be positioned so that it is difficult for the operator to access the injector to load a syringe thereon. Moreover, injector heads are typically not securely anchored and can move during syringe loading, further complicating loading of a syringe thereon.

It is very desirable to develop new syringes, injectors, injector systems and methods to reduce operator time/involvement in loading the syringe onto the injector and/or in connecting the syringe plunger to the injector drive member, while ensuring secure engagement between the syringe (including the syringe plunger) and the injector.

SUMMARY OF THE INVENTION

The present invention provides improved injectors, injector systems, syringes and methods in which the syringe is loaded upon and/or unloaded from the injector in a powered or manual manner. The loading/connecting features of the present invention greatly simplify the process of loading a front-loading syringe onto an injector and frees valuable operator time to accomplish other tasks.

The powered loading features of the present invention also provide greater confidence of proper and secure engagement of the syringe to the injector and/or the syringe plunger to the injector drive member. Moreover, because the loading procedure is powered, tighter tolerances can be designed into the mounting and retaining mechanisms of the present invention than with previous front-loading systems in which tolerances were limited or loosened to facilitate manual loading. The tighter tolerances of the present invention substantially reduce or eliminate play or movement of the syringe after connection thereof to the injector, thereby facilitating more accurate control of the injector.

In one aspect, the present invention provides an injector for injecting a fluid from a syringe. The syringe includes an elongated body and a mounting member positioned on a rear portion of the body. The syringe further includes a plunger moveably positioned within the body of the syringe. The injector includes a housing having a front wall and a retainer on the front wall. The retainer is adapted to cooperate with the mounting member to retain the syringe on the front wall of the injector. Preferably, the syringe is releasably retained upon the front wall of the injector. The retainer includes a powered loader adapted to bring the mounting member and the retainer into secure engagement to securely connect the syringe to the injector. The injector further includes a powered drive member in the housing. The drive member is adapted to engage the plunger and control the movement of the plunger.

The mounting member of the syringe may be formed integrally with the remainder of the syringe in, for example, a polymer molding procedure. Alternatively, the mounting member may be formed separately from the syringe and attached thereto. For example, an adapter including the mounting member can be fabricated to be separate from and attachable to a syringe body. The adapter can, for example, be designed to accept a syringe such as disclosed in U.S. Pat. No. 5,383,858 to adapt that syringe or other syringes for use in the present invention. Preferably, the adapter is releasably connectible to the injector. The adapter is also preferably releasably connected or attached to the syringe.

Likewise, syringes for use in the present invention are readily adapted for use with other injectors through use of an adapter. Such an adapter can, for example, be used to load a syringe of the present invention on an injector as disclosed in U.S. Pat. No. 5,383,858.

In several embodiments, the powered loader of the present invention moves one or more components of the retainer to engage the mounting member and to bring the mounting member and the retainer into secure connection, thereby securely connecting the syringe to the injector. For example, the mounting member may include threading and the retainer may include a cooperating threaded member. The powered loader may rotate the threaded member of the retainer relative to the threading on the syringe to engage the threading on the syringe and securely connect the syringe to the injector.

In general, many types of cooperating attachment members can be used for the mounting member and the retainer. The mounting member may, for example, include a mounting flange or flanges (for example, a single annular flange or a plurality of flanges positioned about the circumference of a syringe or adapter) and the retainer may include a cooperating retaining flange or flanges. In this embodiment, the powered loader preferably moves the retainer to cause the retainer flange(s) to engage the mounting flange(s) to securely connect the syringe to the injector.

The injector may also include a loading or mounting sensor to determine when the syringe is in position for the powered loader to bring the mounting member and the retainer into secure engagement. The powered loading procedure can thereby be automatically initiated when the syringe is in position. The injector may also include one or more sensors to read information encoded upon the syringe. In another embodiment, a single sensor can be used to both read encoded syringe information and to initiate the powered loading process.

The syringe (or an adapter that is attached to the rear of the syringe as described above) may include a generally annular flange preferably positioned forward of the mounting flange(s) that forms a sealing engagement with a forward surface of the retainer to assist in creating a secure engagement of the syringe to the injector and to assist in preventing leakage of fluids into the injector.

Preferably, the drive member of the injector includes an engagement member on a forward end thereof. The engagement member is preferably adapted to connect or dock to the plunger upon forward advancement of the drive member. Preferably, the engagement member is suitable to connect to the plunger regardless of the axial position of the plunger within the syringe and regardless of the relative angular positions of the drive member and plunger about a generally common axis. Preferably, the drive member automatically connects to the plunger either during or shortly after the power loading or manual loading of the syringe onto the injector.

The drive member may, for example, be automatically advanced forward upon loading of the syringe on the injector to connect the drive member to the plunger. Whether the drive member is connected to the plunger automatically or by manual control, the injector preferably controls the motion of the drive member based upon syringe information encoded upon the syringe. For example, if the injector determines that the syringe is empty from the syringe information encoded upon the syringe, the injector preferably causes the drive member to advance the plunger forward to expel air from the syringe in preparation for loading the syringe with fluid. However, if the injector determines that the syringe is prefilled from the syringe information encoded upon the syringe, the injector preferably stops forward advancement of the drive member upon connection of the drive member with the plunger to prevent undesirable expelling of injection fluid. Controlling the drive member, for example, to perform certain preinjection procedures in a manner that depends upon the type of syringe loaded upon the injector can save valuable user time and helps standardize injection procedures.

In another aspect, the present invention provides a system for injecting a liquid medium that includes a front-loading syringe for injecting a fluid into a patient and a powered injector. The syringe preferably includes: an elongated body; a mounting member positioned on a rear portion of the body, and a plunger moveably positioned within the body of the syringe. The injector preferably includes: a housing having a front wall and a retainer on the front wall that is adapted to retain the syringe on the front wall. The retainer preferably includes a powered loader adapted to bring the mounting member and the retainer into secure engagement to securely connect the syringe to the injector. The injector further includes a powered drive member in the housing that is adapted to engage the plunger and control the movement of the plunger.

In a further aspect, the present invention provides a method of connecting a front-loading syringe to a powered injector including the steps of: positioning the syringe in a mounting position on the injector; and moving a retaining member of the injector in a powered manner to engage the syringe and connect the syringe to the injector.

In another aspect, the present invention provides a syringe for use with a powered injector including: an elongated body, a plunger moveably positioned within the body of the syringe, and a threaded mounting member positioned on a rear portion of the syringe to retain the syringe on the injector. The syringe preferably further includes a stop member to prevent rotation of the syringe relative to a threaded retaining member of the injector when the threaded retaining member is rotated relative to the threaded mounting member to engage the threaded mounting member and connect the syringe to the injector.

In a further aspect, the present invention provides an injector for injecting a fluid from a syringe. The syringe includes an elongated body, a mounting member positioned on a rear portion of the body, a plunger moveably positioned within the body of the syringe, and encoded syringe information. The injector preferably includes: a sensor to read the encoded syringe information and a powered drive member adapted to engage the plunger and control the movement of the plunger. The drive member preferably controls the movement of the plunger in accordance with the encoded syringe information.

In still another aspect, the present invention provides a method of connecting a syringe to an injector for injection of a fluid into a patient, the syringe including a plunger positioned therein and encoded syringe information. The method includes the steps of: connecting the syringe to the injector; having the injector read the syringe information;

and having the injector control the motion of the plunger in a manner that is dependent upon the encoded syringe information.

BRIEF DESCRIPTION OF THE DRAWINGS

Other aspects of the invention and their advantages will be discerned from the following detailed description when read in connection with the accompanying drawings, in which:

FIG. 4A illustrates a side view of an embodiment of a plunger, retainer, piston and plunger release mechanism in which the piston is engaged by the plunger.

FIG. 4B illustrates a side view of the plunger, retainer, piston and plunger release mechanism of FIG. 4A in which the plunger release mechanism has been advanced to allow disengagement of the plunger from the piston.

DETAILED DESCRIPTION OF THE INVENTION

Figure 1:
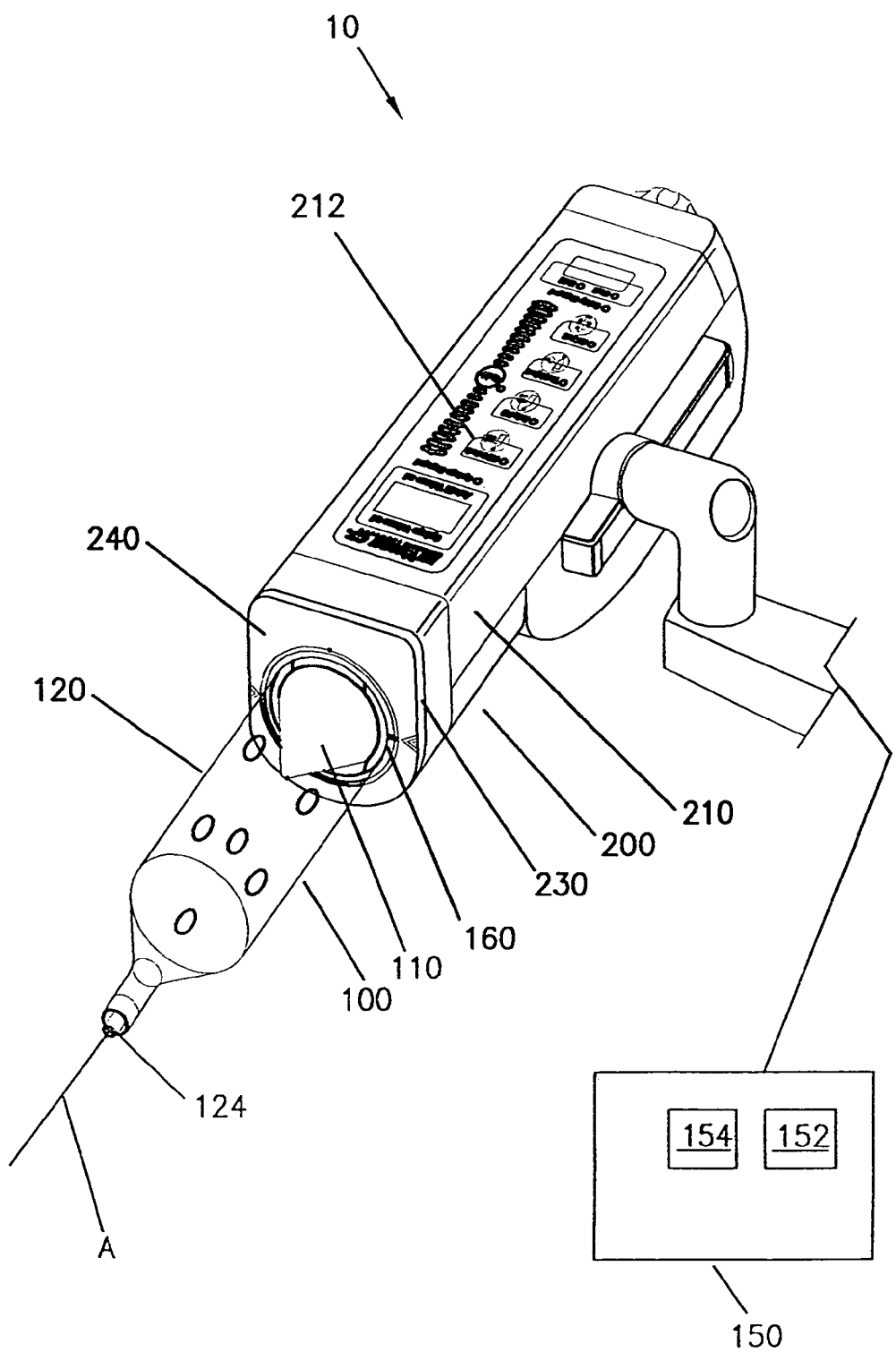
FIG. 1 illustrates a front perspective view an embodiment of an injector system of the present invention.

An embodiment of a front-loading injector system 10 of the present invention is illustrated in FIGS. 1 through 4D. Injector system 10 includes a syringe 100 and an injector 200. Injector housing 210 of injector 200 preferably includes a reciprocating piston 220 (see, for example, FIGS. 4A and 4C) therein which cooperates with a syringe plunger 110 disposed within an elongated cylindrical body 120 of syringe 100 to inject an injection fluid (for example, a liquid contrast medium) from the interior of syringe 100 into a patient. Piston 220 is preferably extendible and retractable via a powered means as known in the art (not shown) that is preferably contained within injection housing 210 and includes, for example, a motor or hydraulic system, including appropriate gearing (not shown). As also known in the art, injector 200 also preferably includes a motor controller for controlling operation of a motor and thereby controlling operation of piston 220. The operation of injector 200 can, for example, be controlled by a computer 150 including a processing unit 152 and memory 154.

As used herein to describe system 10, the terms "axial" or "axially" refer generally to an axis A around which system 10 (including, for example, piston 220 and syringe 10) is preferably formed (although not necessarily symmetrically therearound). The terms "proximal" or "rearward" refer generally to an axial direction toward the end of injector housing 210 opposite the end to which syringe 10 is mounted. The terms "distal" or "forward" refer generally to an axial direction toward a syringe tip 124 of syringe 10. The term "radial" refers generally to a direction normal to axis A.

Piston 220 moves axially forward and rearward through an opening 232 in a retainer 230 that includes a face plate 240 that is attached to or formed integrally with the front wall of housing 210. As illustrated in FIGS. 1 through 3, retainer 230 preferably further includes a generally annular retaining member 250 that rotatably seats in a seating area 234 in retainer 230. Retaining member 250 may, for example, include threading 252 on an inner surface thereof. Threading 252 cooperates with threading 130 positioned on a rearward portion of syringe body 120 to load and retain syringe 100 on injector 200.

During loading of syringe 100 onto injector 200, an operator inserts the rear portion of syringe 100 within opening 232 in face plate 240 so that, for example, one or more guide or stop members 140 are aligned with corresponding slot(s) 260 formed in face plate 240. Retainer 230 may include a sensor bank 264 (seated, for example, in seating area 266 formed in face plate 240) including a loading sensor or sensors 270 to sense the presence of syringe 100 and begin rotation of retaining member 250 to draw syringe 100 rearward with the opening in face plate 240 and create a secure engagement between syringe 100 and injector 200. Many types of sensors as known in the art can be used as loading sensor(s) 270. For example, loading sensor 270 can include a switch mechanism that is triggered by contact with stop member 240. Alternatively, a manual switch (not shown) located on injector 200 or remote therefrom can be used to begin rotation of retaining member 250 once syringe 100 is in position.

Figure 2A:
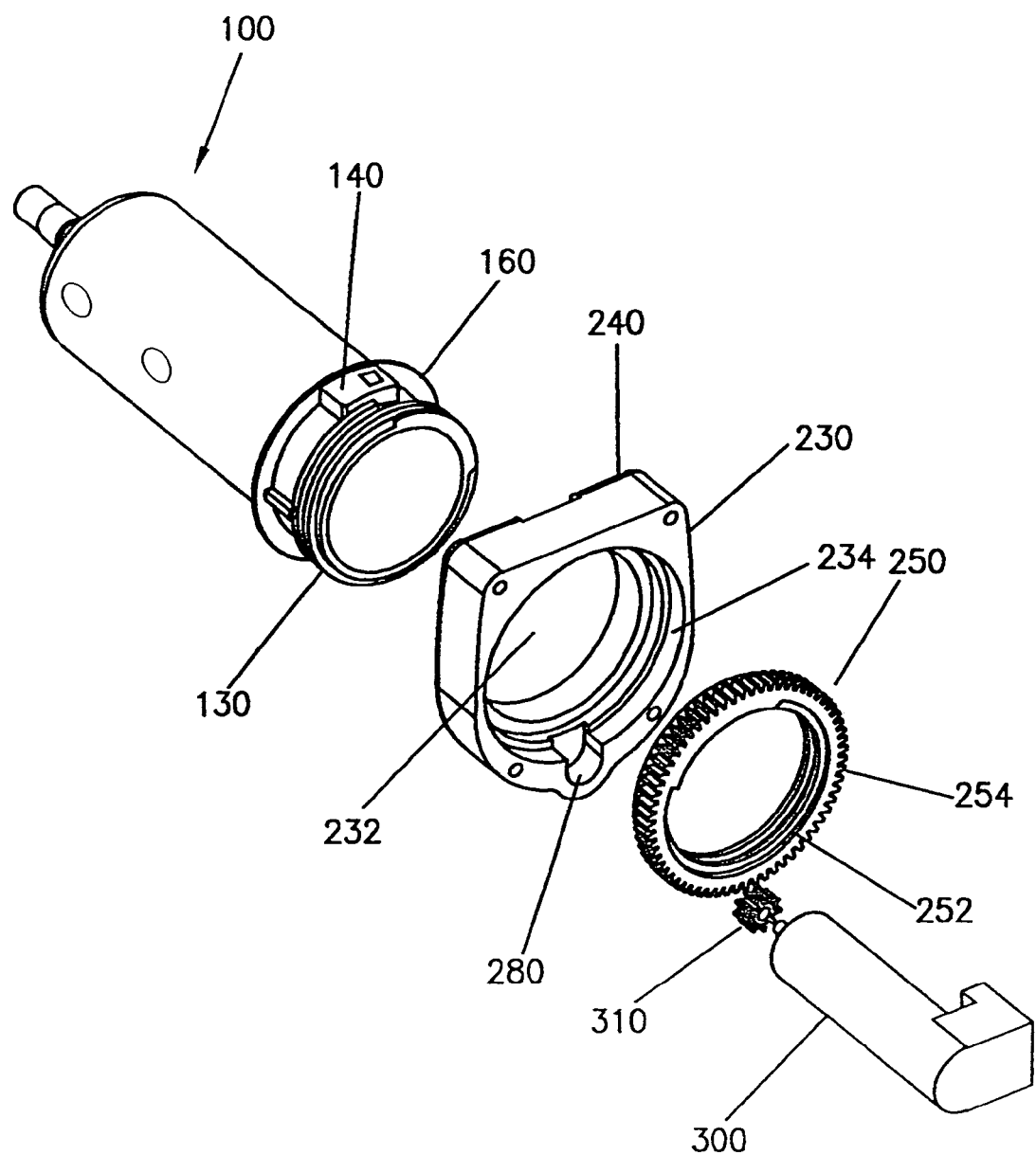
FIG. 2A illustrates a rear perspective view of an embodiment of a syringe and injector retainer in a disassembled state.
Figure 2B:
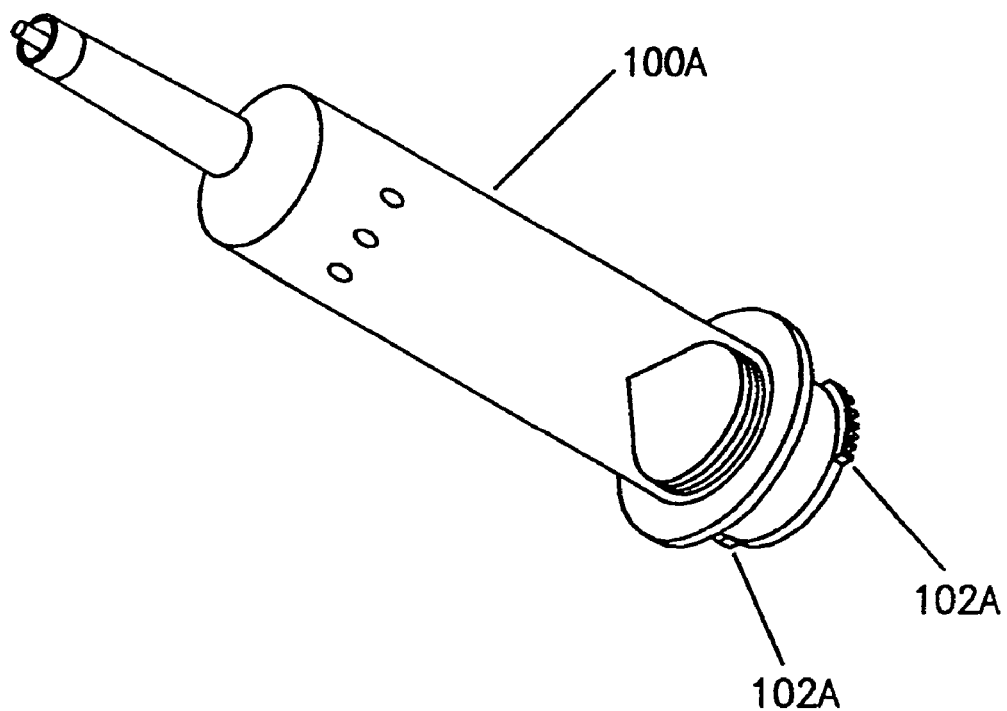
FIG. 2B illustrates a rear perspective view of a syringe and an adapter in a disassembled state.
Figure 2B:
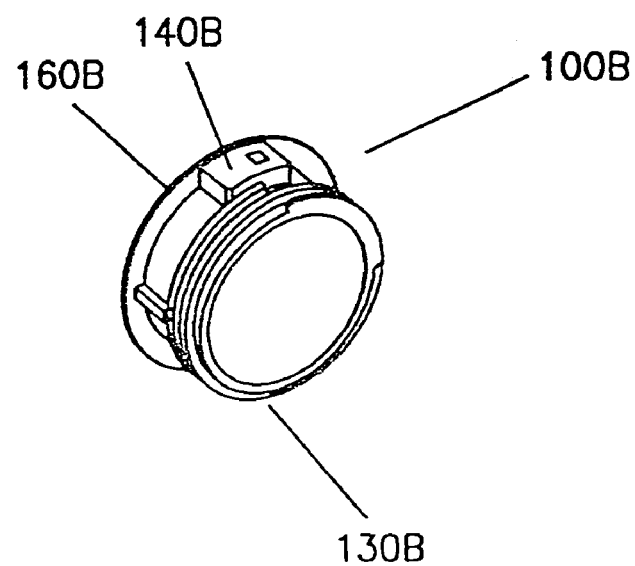
Figure 3:
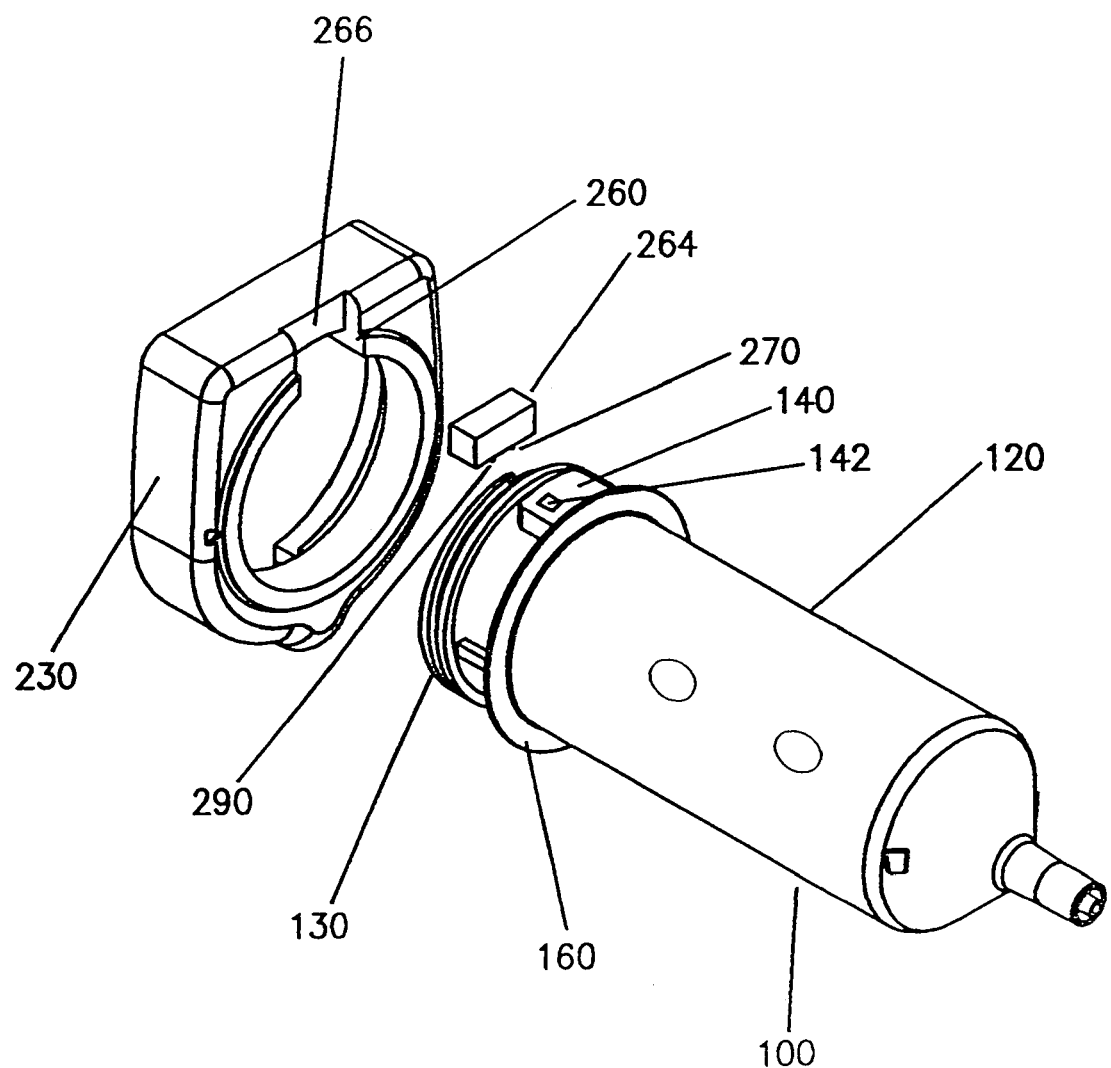
FIG. 3 illustrates a front perspective view of the syringe and retainer of FIG. 2A in a disassembled state.

FIG. 2B illustrates another embodiment of a syringe 100A which cooperates with an adapter 100B to connect to retainer. Adapter 100B preferably includes threading 130B, a guide or stop member 140B and a flange 160B that cooperate with retainer 230 as described above. Syringe 100A may, for example, be a syringe as disclosed in U.S. Pat. No. 5,383,858 that connects to adapter 100B in the manner that is described in U.S. Pat. No. 5,383,858 for connection of syringe 100A to the injector of U.S. Pat. No. 5,383,858. In that regard, adapter 100B includes retaining flanges (not shown) for receiving mounting flanges 102A on the rearward end of the syringe 100A. Syringe is manually rotated to engage the mounting flanges behind the associated or cooperating flanges on the adapter. Use of an adapter such as adapter 100B enables use of a wide variety of syringes with the retainers of the present invention. With use of an adaptor, many types of syringes can be used to take advantage of the benefits of the injectors of the present invention.

Figure 2C:
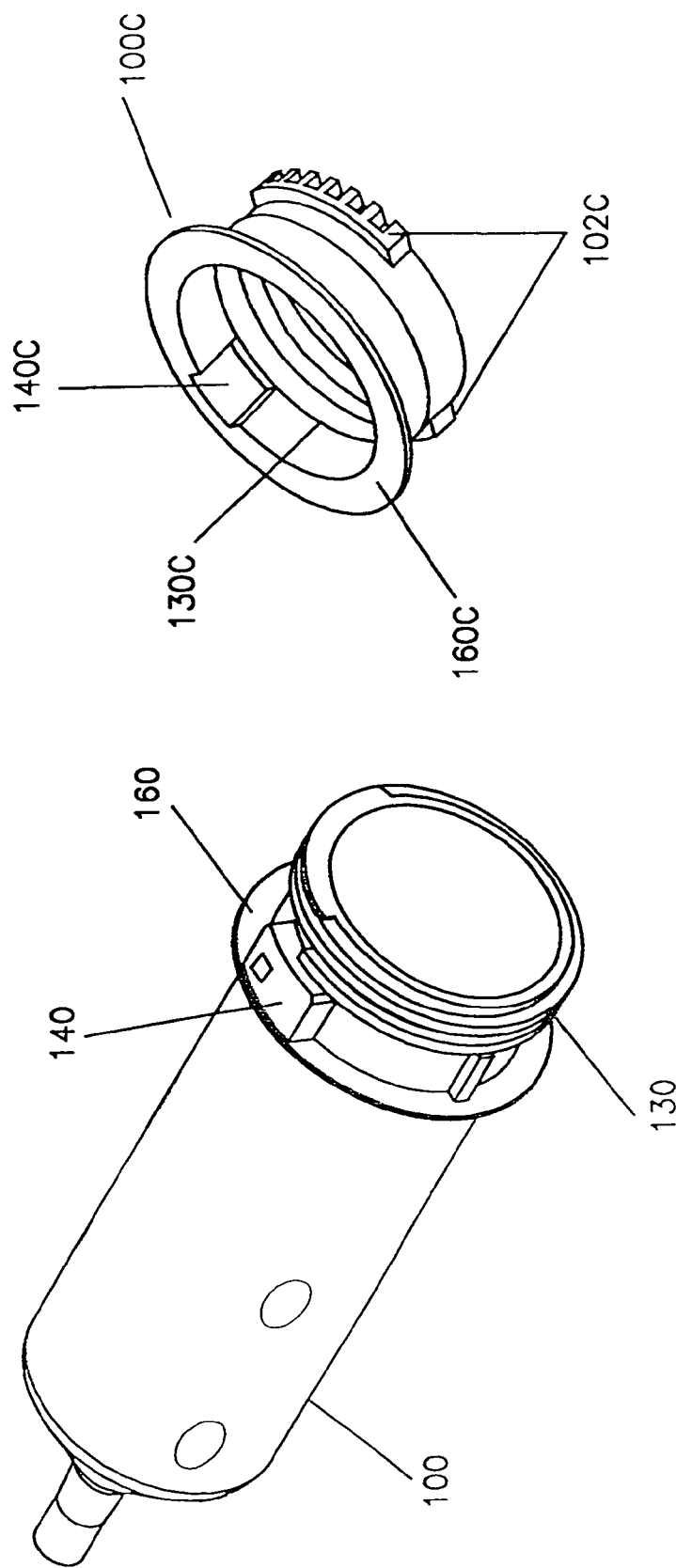
FIG. 2C illustrates a rear perspective view of a syringe and an adapter in a disassembled state.

Similarly, syringe 100 can easily be adapted for use with other injectors through use of an adapter such as adapter 100C illustrated in FIG. 2C. Adapter 100C can, for example, be designed to adapt syringe 100 for use in current manually loaded injectors such as described in U.S. Pat. No. 5,383,858. In that regard, adapter 100C includes on a rearward end thereof retaining flanges 102C that cooperate with the injector of U.S. Pat. No. 5,383,858 as described therein. On a front end thereof, adapter 100C also includes an opening having a slot 140C on the perimeter thereof through which guide member 140 passes to allow threading 130 of syringe 100 to engage threading 130C of adapter 100C to connect syringe 100 to adapter 100C.

Sensor 270 or a manual switch as described above is preferably in communication with a power source such as an electric motor 300 so that motor 300 is switched on when syringe 100 is sensed by sensor 270 or when an operator selects the manually operated loading switch. In the embodiment of FIGS. 1 through 4D, motor 300 is in operative connection with a gear 310 that is rotatably seated within a seating area 280 within retainer 230 to mesh with an outer geared surface 254 of retaining member 250. Rotational motion of motor 300 is thus translated to rotation of rotating member 250. Abutment of stop member 140 with the sides of slot 260 prevents syringe 100 from rotating relative to retaining member 250 when retaining member 250 is rotated to engage syringe threading 130, thereby facilitating threaded engagement between retaining member 250 and syringe 100. Limit switches (not shown), position sensors (not shown) and/or measurement of motor current of motor 300 can, for example, be used to control movement of retaining member 250 to ensure that syringe 100A is properly loaded and excess stresses are not placed thereon.

Using cooperating threaded elements, syringe 100 can be loaded upon injector 200 in either a powered or manual manner. For example, if it is desirable to load syringe 100 onto injector 200 in a manual manner, retaining member 250 can be advanced to its forward position and held in that position. Syringe 100 can then me manually rotated to engage threading 130 with threading 252 of retaining member 250.

Syringe 100 preferably also includes a generally annular flange 160 positioned forward of threading 130. Flange 160 is preferably drawn securely against a portion of a front or forward surface of face plate 240 when syringe 100 is fully engaged within injector 200. Flange 160 assists in forming a secure interference fit and also assists in preventing leakage of fluids into injector 200.

Figure 4C:
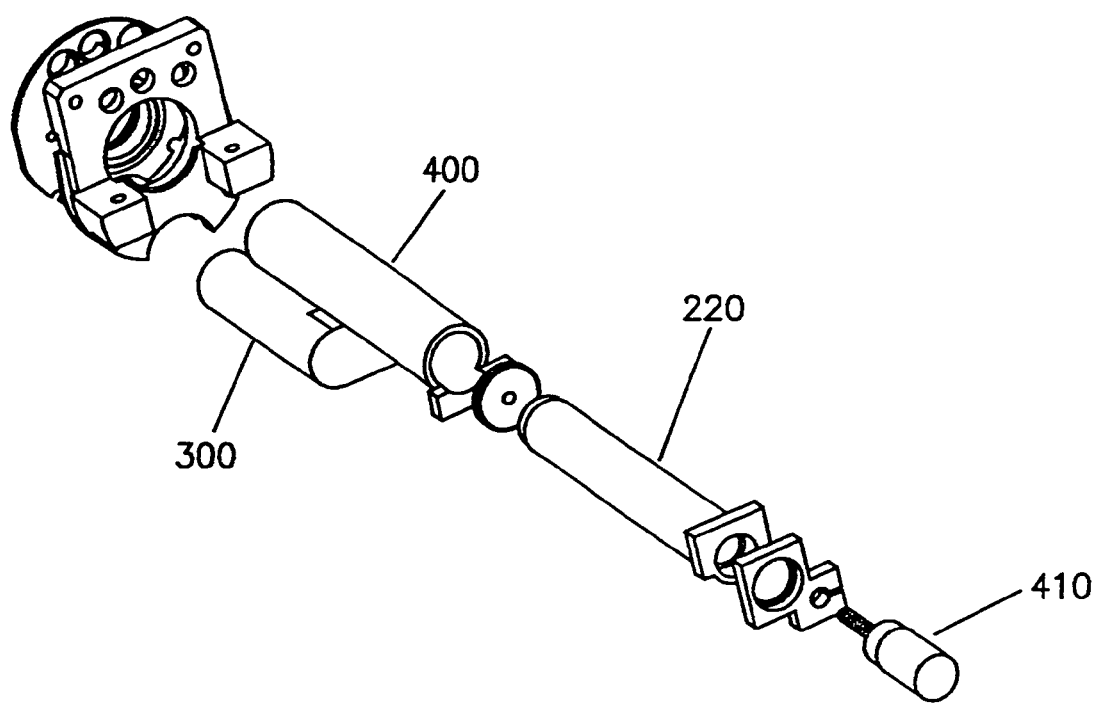
FIG. 4C illustrates a rear perspective view of the piston and plunger release mechanism of FIGS. 4A and 4B in a disassembled state.
Figure 4D:
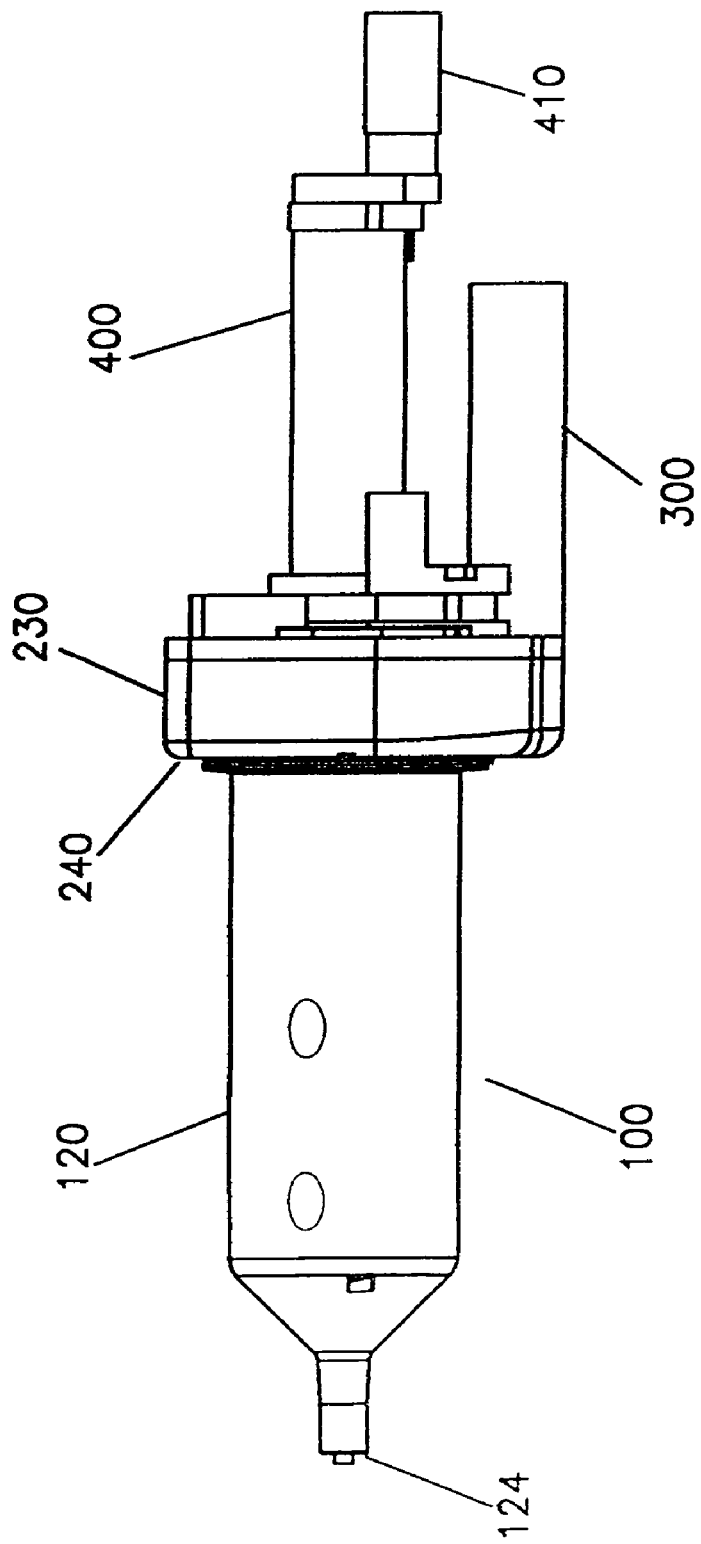
FIG. 4D illustrates a side view of the syringe, retainer, and plunger release mechanism of FIGS. 4A, 4B and 4C.

Upon secure connection of syringe 100 to injector 200 as described above (in either a powered or manual loading procedure), a preferably releasable connection between plunger 110 and piston 220 is preferably made. A number of manners of forming a releasable connection between a plunger and a piston in a front-loading injector system are disclosed in U.S. Pat. Nos. 4,677,980, 5,383,858, 5,873,861 and 5,947,935, the disclosures of which are incorporated herein by reference. In the embodiment illustrated in FIGS. 4A through 4D, plunger 110 includes capture legs 112 that extend rearward from a rear surface of plunger 110. Capture legs 112 include radially inward extending abutment members 114 that cooperate with a radially outward extending flange 224 of a piston head 222 to releasably connect plunger 110 to piston 220. Capture legs 112 are cantilevered such that, when abutment members 114 are contacted by flange 224 upon forward advancement of piston 220 relative to plunger 110, capture legs 112 are forced radially outward to allow piston head 222 to pass therebetween. Capture legs 112 spring radially inward once flange 224 passes abutment members 114 so that abutment members 114 engage flange 224 to releasably connect plunger 110 to piston 220 as illustrated in FIG. 4A. Flange 224 is preferably generally circular in shape so that the relative angular positions (as rotated about the common axis A) of plunger 110 and drive member 220 are unimportant to the ability to connect plunger 110 and drive member 220.

In the embodiment of FIGS. 4A through 4D, plunger 110 is preferably released from piston 220 by forward advancement of a release cylinder 400 that contacts capture legs 112 to force capture legs radially outward as illustrated in FIG. 4B. Piston 220 can then be drawn rearward to release plunger 110 from connection therewith. During operation of injector 200, release cylinder 400 is in a retracted position as illustrated in FIG. 4A and travels generally in unison with piston 220, which is disposed within release cylinder 400. Upon, for example, completion of an injection procedure, an operator can preferably depress a release switch 212 on injector housing 210 to initiate release of plunger 110 (and, preferably, release of syringe 100 from injector 200). Upon depression of switch 212, a plunger release motor 410 is preferably activated to advance release cylinder 400 to release plunger 110.

Upon release of the connection of plunger 110 from piston 220 via release switch 212, syringe 100 can be released from injector 200 by simply activating retaining member 250 to disconnect threading 252 thereof from threading 130 on the rear of syringe 100. Preferably, such activation of retaining member 250 occurs automatically upon release of plunger 100. Upon disconnection, syringe 100 preferably remains releasably seated in opening 232 of retainer 230 until removed by the operator.

Depending, for example, upon the nature of syringe 110, and regardless of whether syringe 100 is loaded in a powered or manual manner, different operations may be performed upon connection of syringe 100 to injector 200. It is particularly advantageous to control and/or automate certain preinjection procedures. For example, in the case of an empty syringe, it may be desirable to advance plunger 110 within syringe 100 to expel air therefrom and, subsequently, to draw injection fluid into syringe 100. One or more of these steps may be accomplished through manual control by an operator or automatically via, for example, control from computer 150.

In the case of a prefilled syringe, on the other hand, after connection of syringe 100 to injector 200, caution should be exercised in advancing piston 220 any farther forward than required to connect piston 220 to plunger 110. Excess forward motion of piston 110 will result in expelling injection fluid in a prefilled syringe.

Although the determination of the type of syringe connected to injector 200 can be made by the operator and injector 200 controlled appropriately, it is also possible to have injector 200 detect the type of syringe 100, the contents thereof, the volume thereof etc. In that regard, one or more sensors 290 can be positioned on retainer 230 to detect syringe information that can be encoded on, for example, area 142 on syringe 100 (see FIG. 3). Methods and systems for reading encoded syringe information are disclosed, for example, in U.S. Pat. No. 5,383,858 and PCT International Patent Application Serial No. PCT/US99/13360 filed Jun. 15, 1999, assigned to the assignee of the present invention, the disclosures of which are incorporated herein by reference. In one embodiment, sensors 270 and 290 are combined in a single sensor.

Moreover, in the case that a prefilled syringe is connected to injector 200, the position of syringe plunger 100 may be detected by injector 200 to ensure that piston 220 is not advanced too far forward in connecting piston 220 to plunger 110. The detection of plunger position can be accomplished in numerous ways. For example, motor current in injector 200 can be measured. The greater resistance to advancement of piston 220 upon contact thereof with plunger 110 can be sensed by measuring motor current and the advancement of piston 220 stopped. Likewise, a sensor can be placed on piston head 222 and or plunger 110 to detect contact of piston 220 with plunger 110. For example, plunger 110 can include a light source 116 and a light sensor 116' (see FIG. 4B). Connection of drive member 220 with plunger 110 will prevent light from light source 116 from reaching light sensor 116' and thereby provide an indication that connection has been made.

Figure 4E:
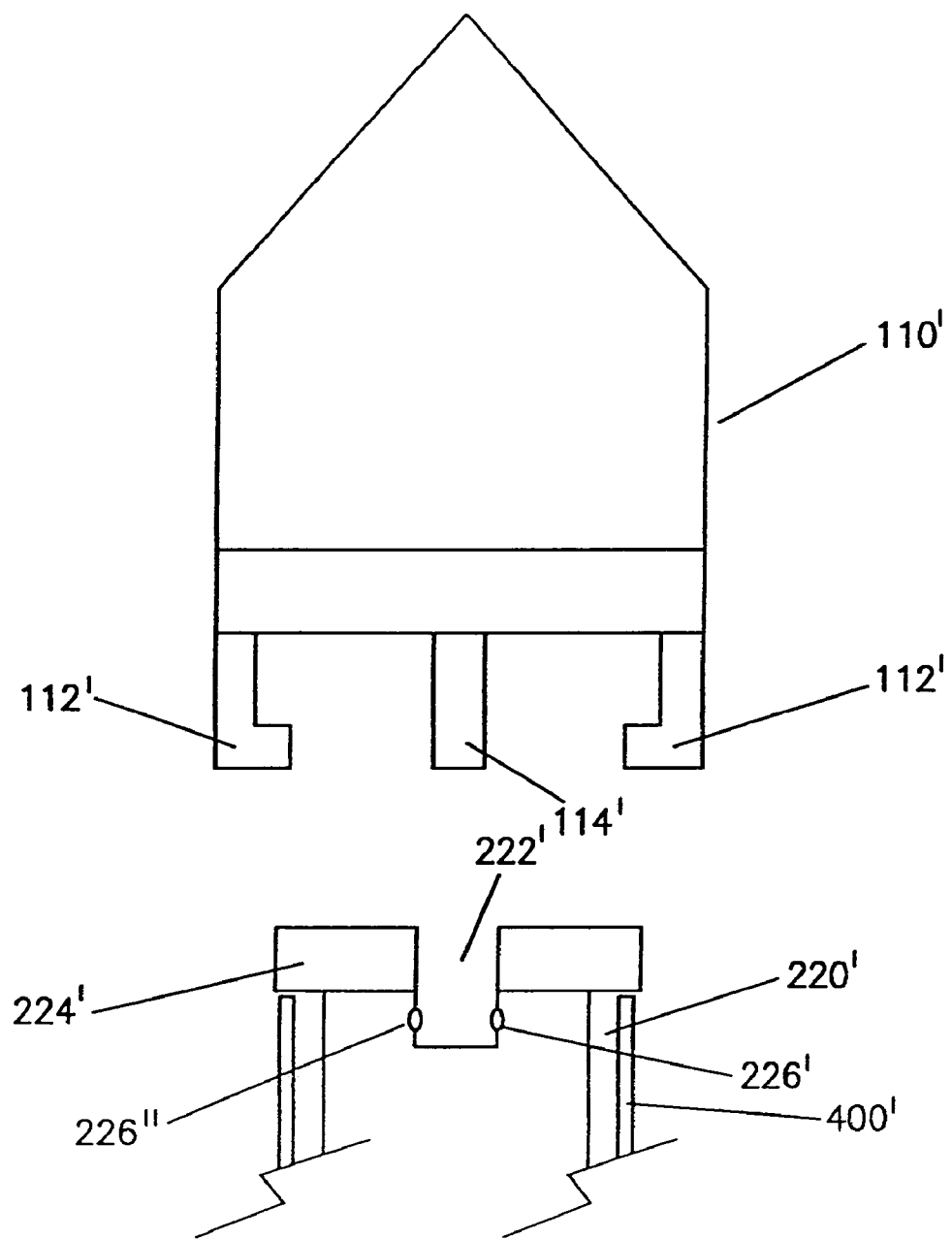
FIG. 4E illustrates a cross-sectional view of an embodiment of a design of a drive member including a sensor to detect plunger position.

FIG. 4E illustrates an alternative embodiment of a plunger 110' having capture members 112'. In this embodiment, plunger 110' includes a rearward projecting element 114' that inserts into a passage 222' of a piston head 224' of a piston 220' upon connection of piston 220' and plunger 110'. Disposed on one side of passage 222' is a light source 226', and on an opposing side thereof is a light sensor 226". Connection of drive member 220' with plunger 110' will cause projecting element 114' to enter passage 222' and prevent light from light source 226' from reaching light sensor 226", thereby providing an indication that connection has been made.

During loading of syringe 100 onto injector 200 as described above, an operator inserts the rear portion of syringe 100 within opening 232. Loading sensor(s) 270 sense the presence of syringe 100 and begin loading syringe 100 upon injector 200. The type of syringe is sensed by sensor 290. Docking of piston 220 to plunger 110, as described above, is preferably automatically initiated upon loading of syringe 100 into injector 200. If injector 200 senses that an empty syringe has been loaded thereupon, injector 200 preferably advanced piston 220 to engage plunger 110. After engagement of plunger 110, piston 220 preferably continues to advance forward to expel air from syringe 100 and prepare syringe 100 for filling with injection fluid. Should injector 200 sense that a prefilled syringe has been loaded thereupon, however, piston 220 preferably engages plunger 110 and discontinues any further advancement until an injection procedure begins.

Figure 5A:
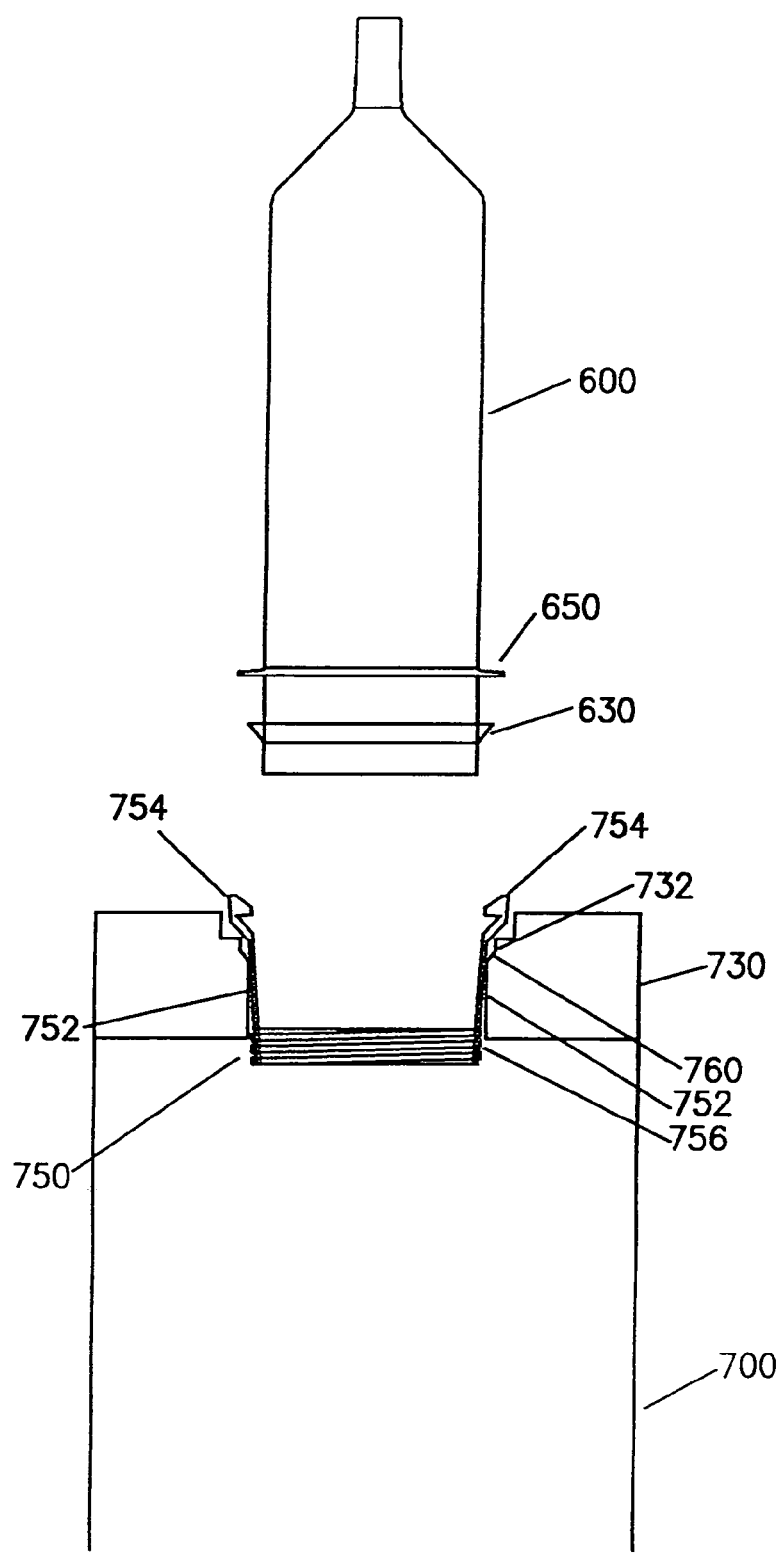
FIG. 5A illustrates a cross-sectional view of another embodiment of an injector system of the present invention in which the syringe is being brought into position for loading upon the injector.
Figure 5B:
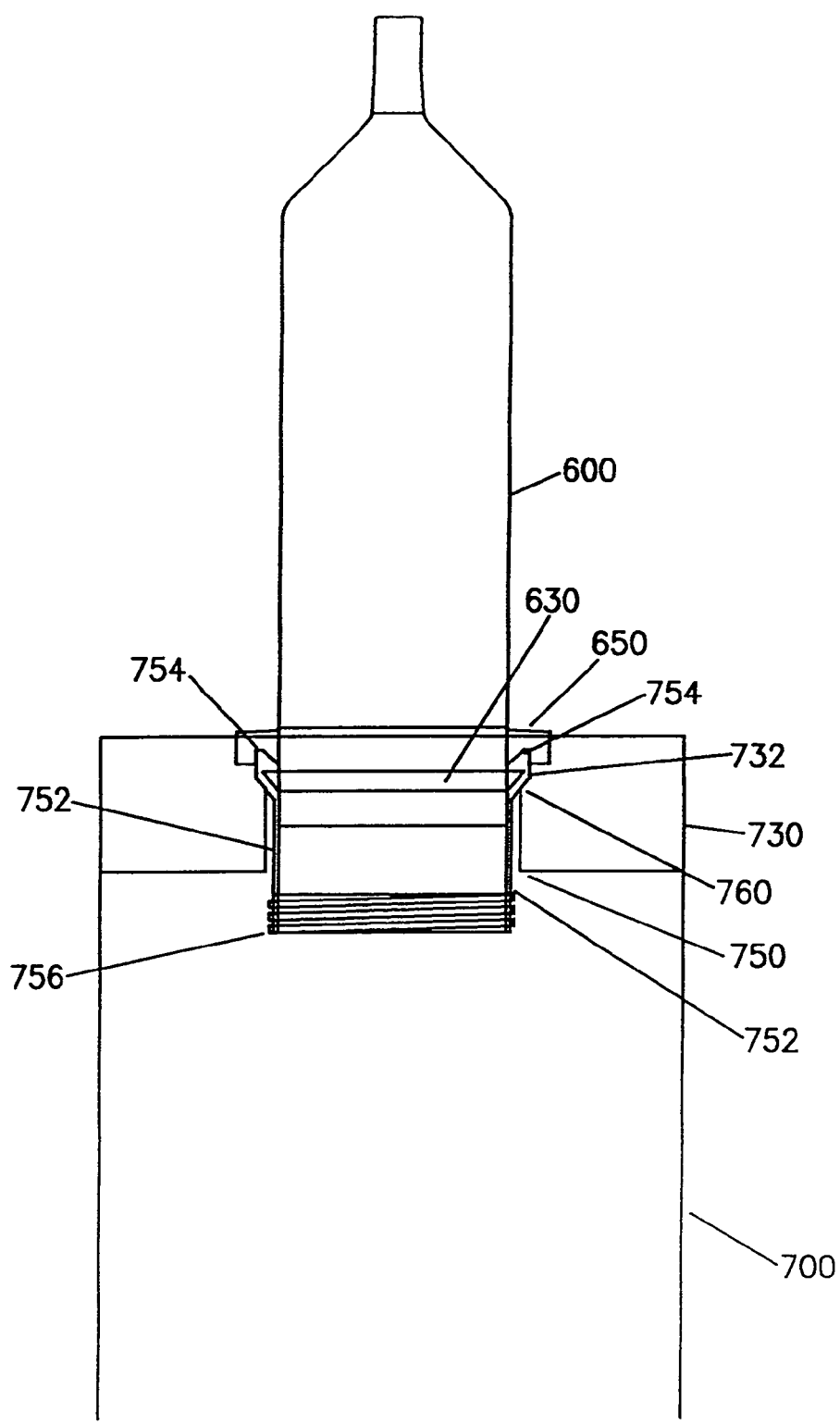
FIG. 5B illustrates a cross-sectional view of the embodiment of FIG. 5A in which the syringe is in secure connection with the injector.

An alternative embodiment of a syringe mounting and retaining mechanism is illustrated in FIGS. 5A and 5B. In this embodiment, syringe 600 includes a generally annular mounting flange 630 formed on a rearward portion thereof. Syringe 600 also includes a generally annular flange or sealing member 650 formed forward of mounting flange 630. Injector 700 includes a retainer 730 to securely connect syringe 600 to injector 700. Retainer 730 includes, for example, a retaining member 750. Retaining member 750 preferably includes a plurality of capture members 752 that are preferably positioned around the circumference of retaining member 750. Each of capture members 752 preferably includes an abutment member 754 on a forward end thereof that is adapted to form an abutting connection with mounting flange 730.

Before loading of syringe 600 on injector 700, capture members 752 are in an open position as illustrated in FIG. 5A in which capture members 752 are flared radially outward so that mounting flange 630 can pass by abutment members 754. Once syringe 600 is placed in loading position by an operator, retaining member 750 is drawn rearward, for example, via cooperation of threading 756 with a cooperating threaded member (not shown). As retaining member 750 is drawn rearward, the radially outer edges of capture members 652 contact a radially inward extending surface 732 of retainer 730, thereby drawing abutment members 754 radially inward to engage mounting flange 630.

After abutment members 754 engage mounting flange 630 and retainer 650 is drawn further rearward, syringe 600 is drawn rearward until flange 650 is drawn into secure engagement with a front surface of retainer 630 as illustrated in FIG. 5B. Sensors (not shown) can be provided to ensure that secure engagement has been achieved. Capture members 752 and abutment members 754 are preferably forced radially inward by abutment with a beveled or chamfered surface 760 of retainer 730. Syringe 600 is thereby securely engaged within injector 300. To release syringe 600, retaining member 650 is moved forward so that capture members 752 are allowed to expand in a radial outward manner as illustrated in FIG. 5A.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. An injector for injecting a fluid from a syringe comprising a body, a plunger moveably positioned within the body, and encoded syringe information, the injector comprising:
   a motor;
   a controller operably associated with the motor;
   a sensor operably associated with the controller and operable to read the encoded syringe information when the syringe is attached to the injector;
   a drive member powered by the motor and operable to automatically advance and engage the plunger when the sensor reads the encoded syringe information; and
   a plunger engagement detection device operable to determine when the drive member of the injector has engaged the plunger of the syringe.

2. The injector of claim 1 wherein the drive member includes an engagement member on a forward end thereof, the engagement member adapted to connect to the plunger upon forward advancement of the drive member.

3. The injector of claim 1 wherein the injector controller determines that the syringe is empty from the syringe information encoded upon the syringe and causes the drive member to fully advance the plunger forward within the syringe body to expel air from the syringe.

4. The injector of claim 1 wherein the injector controller determines that the syringe is prefilled from the syringe information encoded upon the syringe and substantially stops forward advancement of the drive member upon engagement of the drive member with the plunger.

5. The injector of claim 1 wherein the plunger engagement detection device comprises a sensor disposed on the plunger, the sensor operable to detect engagement of the drive member with the plunger.

6. The injector of claim 5 wherein the sensor comprises a light source and a light sensor.

7. The injector of claim 6 wherein engagement of the drive member with the plunger substantially prevents light from the light source from reaching the light sensor, thereby indicating that the drive member has engaged the plunger.

8. The injector of claim 6 wherein the plunger comprises two capture members extending rearward therefrom, the light source being disposed on one capture member and the light sensor being disposed on the other capture member.

9. The injector of claim 8 wherein engagement of the drive member with the plunger substantially prevents light from the light source from reaching the light sensor, thereby indicating that the drive member has engaged the plunger.

10. The injector of claim 1 wherein the plunger engagement detection device comprises a sensor disposed on the drive member or the plunger.

11. A method of connecting a syringe comprising a plunger and encoded syringe information to an injector comprising a motor, a controller operably associated with the motor, a sensor operably associated with the controller, a drive member powered by the motor and a plunger engagement detection device, the method comprising:
connecting the syringe to the injector;
reading the syringe information encoded on the syringe;
automatically advancing the drive member of the injector when the sensor reads the syringe information encoded upon the syringe; and
determining when the drive member of the injector has engaged the plunger of the syringe.

12. The method of claim 11, further comprising:
determining that the syringe is empty from the syringe information encoded upon the syringe; and
fully advancing the plunger forward to expel air from the syringe in preparation for loading the syringe with fluid.

13. The method of claim 12, further comprising:
retracting the plunger to load fluid into the syringe.

14. The method of claim 13, further comprising:
advancing the plunger to inject fluid into a patient connected to the syringe.

15. The method of claim 11, further comprising:
determining that the syringe is prefilled from the syringe information encoded upon the syringe; and
substantially stopping forward advancement of the drive member upon engagement of the drive member with the plunger to prevent expulsion of fluid from the syringe.

16. The method of claim 15, further comprising:
advancing the plunger to inject fluid into a patient connected to the syringe.

17. The injector of claim 1 wherein the injector controller substantially stops advancement of the drive member upon engagement of the drive member with the plunger of the syringe.

18. The injector of claim 1 wherein the plunger engagement detection device comprises a sensor disposed on the drive member, the sensor operable to detect engagement of the drive member with the plunger.

19. The injector of claim 18 wherein the sensor comprises a light source and a light sensor.

20. The injector of claim 19 wherein engagement of the drive member with the plunger substantially prevents light from the light source from reaching the light sensor, thereby indicating that the drive member has engaged the plunger.

21. The injector of claim 19 wherein the drive member comprises a forward end defining a passage therein having opposing sidewalls, the light source being disposed on one sidewall of the passage and the light source being disposed on the other sidewall of the passage.

22. The injector of claim 21 wherein the plunger comprises a rearward projecting element operable to extend into the passage when the drive member engages the plunger, the rearward projecting element operable to substantially prevent light from the light source from reaching the light sensor, thereby indicating that the drive member has engaged the plunger.

23. The method of claim 11, further comprising:
substantially stopping forward advancement of the drive member upon engagement of the drive member with the plunger of the syringe.

24. An injector for injecting a fluid from a syringe comprising a body, a plunger moveably positioned within the body, and encoded syringe information, the injector comprising:
a motor,
a controller operably associated with the motor;
a first sensor operably associated with the controller and operable to read the encoded syringe information when the syringe is attached to the injector;
a drive member powered by the motor and operable to automatically advance and engage the plunger when the first sensor reads the encoded syringe information; and
a sensor disposed on the drive member and operable to detect engagement of the drive member with the plunger.

25. The injector of claim 24 wherein the second sensor comprises a light source and a light sensor.

26. The injector of claim 25 wherein engagement of the drive member with the plunger substantially prevents light from the light source from reaching the light sensor, thereby indicating that the drive member has engaged the plunger.

27. The injector of claim 25 wherein the drive member comprises a forward end defining a passage therein having opposing sidewalls, the light source being disposed on one sidewall of the passage and the light source being disposed on the other sidewall of the passage.

28. The injector of claim 27 wherein the plunger comprises a rearward projecting element operable to extend into the passage when the drive member engages the plunger, the rearward projecting element operable to substantially prevent light from the light source from reaching the light sensor, thereby indicating that the drive member has engaged the plunger.

29. An injector for use with a syringe comprising a body, a plunger moveably positioned within the body, and encoded syringe information, the injector comprising:
a motor;
a controller operably associated with the motor;
a sensor operably associated with the controller and operable to read the encoded syringe information when the syringe is attached to the injector;
a drive member powered by the motor and operable to automatically advance and engage the plunger when the sensor reads the encoded syringe information; and
a plunger engagement detection device operable to determine when the drive member of the injector has engaged the plunger of the syringe,
wherein the injector controller determines that the syringe is empty from the syringe information encoded upon the syringe and causes the drive member to advance the plunger forward within the syringe body to expel air from the syringe.

30. The injector of claim 29 wherein the plunger engagement detection device comprises a sensor disposed on the drive member, the sensor operable to detect engagement of the drive member with the plunger.

31. The injector of claim 30 wherein the sensor comprises a light source and a light sensor.

32. The injector of claim 31 wherein engagement of the drive member with the plunger substantially prevents light from the light source from reaching the light sensor, thereby indicating that the drive member has engaged the plunger.

33. The injector of claim 29 wherein the plunger engagement detection device comprises a sensor disposed on the plunger, the sensor operable to detect engagement of the drive member with the plunger.

34. The injector of claim 29 wherein the plunger engagement detection device comprises a sensor disposed on the drive member or the plunger.

35. An injector for use with a syringe comprising a body, a plunger moveably positioned within the body, and encoded syringe information, the injector comprising:
  a motor;
  a controller operably associated with the motor;
  a sensor operably associated with the controller and operable to read the encoded syringe information when the syringe is attached to the injector;
  a drive member powered by the motor and operable to automatically advance and engage the plunger when the sensor reads the encoded syringe information; and
  a plunger engagement detection device operable to determine when the drive member of the injector has engaged the plunger of the syringe,
  wherein the injector controller determines that the syringe is prefilled with fluid from the syringe information encoded upon the syringe and substantially stops forward advancement of the drive member upon engagement of the drive member with the plunger.

36. The injector of claim 35 wherein the plunger engagement detection device comprises a sensor disposed on the plunger, the sensor operable to detect engagement of the drive member with the plunger.

37. The injector of claim 35 wherein the plunger engagement detection device comprises a sensor disposed on the drive member or the plunger.

38. The injector of claim 35 wherein the plunger engagement detection device comprises a sensor disposed on the drive member, the sensor operable to detect engagement of the drive member with the plunger.

39. The injector of claim 38 wherein the sensor comprises a light source and a light sensor.

40. The injector of claim 39 wherein engagement of the drive member with the plunger substantially prevents light from the light source from reaching the light sensor, thereby indicating that the drive member has engaged the plunger.

41. A method of connecting a syringe comprising a plunger and encoded syringe information to an injector comprising a motor, a controller operably associated with the motor, a sensor operably associated with the controller, a drive member powered by the motor and a plunger engagement detection device, the method comprising:
  connecting the syringe to the injector;
  reading the syringe information encoded on the syringe;
  automatically advancing the drive member of the injector when the sensor reads the syringe information encoded upon the syringe;
  determining when the drive member of the injector has engaged the plunger of the syringe;
  determining that the syringe is empty from the syringe information encoded upon the syringe; and
  advancing the plunger forward to expel air from the syringe in preparation for loading the syringe with fluid.

42. The method of claim 41, further comprising:
  retracting the plunger to load fluid into the syringe.

43. The method of claim 42, further comprising:
  advancing the plunger to inject fluid into a patient connected to the syringe.

44. A method of connecting a syringe comprising a plunger and encoded syringe information to an injector comprising a motor, a controller operably associated with the motor, a sensor operably associated with the controller, a drive member powered by the motor and a plunger engagement detection device, the method comprising:
  connecting the syringe to the injector;
  reading the syringe information encoded on the syringe;
  automatically advancing the drive member of the injector when the sensor reads the syringe information encoded upon the syringe;
  determining when the drive member of the injector has engaged the plunger of the syringe;
  determining that the syringe is prefilled with fluid from the syringe information encoded upon the syringe; and
  substantially stopping forward advancement of the drive member upon engagement of the drive member with the plunger to prevent expulsion of fluid from the syringe.

45. The method of claim 44, further comprising:
  advancing the plunger to inject fluid into a patient connected to the syringe.

* * * * *